US008086303B2

(12) United States Patent
Zhang et al.

(10) Patent No.: US 8,086,303 B2
(45) Date of Patent: Dec. 27, 2011

(54) CARDIAC ARRHYTHMIAS ANALYSIS OF ELECTROPHYSIOLOGICAL SIGNALS BASED ON SYMBOLIC DYNAMICS

(75) Inventors: Hongxuan Zhang, Schaumburg, IL (US); Detlef W. Koertge, Carpentersville, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1046 days.

(21) Appl. No.: 11/956,795

(22) Filed: Dec. 14, 2007

(65) Prior Publication Data

US 2008/0281216 A1     Nov. 13, 2008

Related U.S. Application Data

(60) Provisional application No. 60/917,094, filed on May 10, 2007.

(51) Int. Cl.
*A61B 5/0428* (2006.01)
*A61B 5/0452* (2006.01)

(52) U.S. Cl. .................. 600/515; 600/518; 600/523

(58) Field of Classification Search .......... 600/509, 600/515, 518, 523; 702/19
See application file for complete search history.

(56) References Cited

U.S. PATENT DOCUMENTS

| 6,490,478 B1 | 12/2002 | Zhang |
| 2007/0066906 A1* | 3/2007 | Goldberger et al. .......... 600/509 |
| 2007/0129639 A1 | 6/2007 | Zhang |

OTHER PUBLICATIONS

Zhang et al., "Detecting ventricular tachycardia and fibrillation by complexity measure", IEEE Trans Biomed Eng, 46: 548-55, 1999.
Zhang et al., "Qualitative chaos analysis for ventricular tachycardia and fibrillation based on symbolic complexity", Medical Engineering & Physics, ISSN 1350-4533, vol. 23, No. 8, pp. 523-528, 2001.
Takens, "Detecting strange attractors in turbulence", in: Rand, D.A. and Young, L.S. (Eds) (Springer, Berlin, Heidelberg, New York), pp. 366-387, 1981.
Lempel et al., "On the complexity of finite sequences", IEEE Trans. On IT 22, pp. 75-81, 1976.
Zhang et al., "Complexity measure and complexity rate information based detection of ventricular tachycardia and fibrillation", Medical and Biomedical Engineering and Computing, vol. 38, No. 5, pp. 553-557, 2000.

* cited by examiner

*Primary Examiner* — Carl H. Layno
*Assistant Examiner* — Tammie K Heller
(74) *Attorney, Agent, or Firm* — Alexander J Burke

(57) ABSTRACT

The disclosed method analyzes cardiac electrophysiological signals, including ECG and internal cardiac electrograms, based on multi-level symbolic complexity calculation and multi-dimensional mapping. The results may be used to objectively identify cardiac disorders, differentiate cardiac arrhythmias, characterize pathological severities, and predict life-threatening events. Multi-level symbolization and calculation of the electrophysiological signal is used provide better reliability and analysis resolution for identifying and characterizing cardiac disorders. Adaptive analysis of the cardiac signal complexity enables calculation efficiency and reliability with high SNR, and with low calculation volume and power consumption. One dimension (time or frequency domain) and multi-dimension symbolic analysis is used to provide more information of cardiac pathology and high risk rhythm transition to doctors.

13 Claims, 6 Drawing Sheets

CARDIAC ARRHYTHMIAS ANALYSIS OF ELECTROPHYSIOLOGICAL SIGNALS BASED ON SYMBOLIC DYNAMICS

CROSS-REFERENCE TO RELATED APPLICATIONS

This is a U.S. non-provisional application of U.S. provisional patent application Ser. No. 60/917,094, filed May 10, 2007, by Hongxuan Zhang et al., the entirety of which application is incorporated herein by reference.

FIELD OF THE DISCLOSURE

The disclosure relates to a system and method for monitoring an identification of cardiac arrhythmia, and more particularly to a system and method for application of medical electrophysiological signal analysis to monitoring and identification of cardiac arrhythmia.

BACKGROUND OF THE DISCLOSURE

The timely identification of cardiac arrhythmia can be an important tool in the diagnosis, monitoring and treatment of abnormal heart activity. Current waveform morphologies and time domain parameter analysis of the depolarization and repolarization of the heart, such as P wave, QRS complex, ST segment, and T wave, are used for cardiac arrhythmia monitoring and identification. However, the waveform morphologies and time domain parameter analysis involves with these techniques are sometimes subjective and time-consuming, and require expertise and clinical experience for accurate and proper cardiac rhythm management. Recent efforts have aimed to apply more sophisticated mathematical theories to biomedical signal interpretation, such as frequency analysis, symbolic complexity analysis and nonlinear entropy elevation. Most of these efforts have focused on generating a new pathology index for qualitative cardiac arrhythmia characterization. There are several shortcomings with these clinical investigations and biomedical research strategies.

For example, morphology and time domain index evaluation of the electrophysiological signals are subjective, and can result in inaccurate interpretation and delayed cardiac rhythm management and treatment. Furthermore, there are no criteria of signal morphology evaluation or parameter analysis for intra-cardiac signals and arrhythmia characterization. For example, the threshold of the ST segment changes during intra-cardiac myocardial ischemia/infarction are not 0.1 millivolt (mV) as that in surface ECG signals. Thus, current criteria for ischemia identification and detection is ineffective for intra-cardiac electrograms, and thus new methods are needed for cardiac arrhythmia analysis and detection.

Also, recent research has focused on techniques such as frequency and symbolic analysis to calculate the irregular index of the cardiac signals. It is difficult, however, to map an irregular index onto the severity of the cardiac pathologies, and thus, cardiac arrhythmia analysis and related irregularity calculations have not been successfully used to diagnose and interpret the level and severity of the cardiac pathologies. Furthermore, these research methods have not combined the waveform morphology information, time domain and frequency domain analysis and calculation.

In summary, current clinical methods and research approaches cannot efficiently and automatically differentiate arrhythmias, categorize/map cardiac pathological severities and predict life-threatening disorders. Current clinical methodologies for cardiac arrhythmia calculation and evaluation also may generate inaccurate and unreliable data and results because of unwanted noise and artifacts. Environmental noise and patient movement artifacts, including electrical interference, can distort the waveform and make it difficult to detect R wave and ST segment elevation accurately.

Further, current cardiac applications and methods also cannot efficiently analyze and achieve real time growing trend and prediction of cardiac arrhythmias, such as the pathology trend from low risk to medium, and from medium risk to high risk (severe and fatal) rhythm (especially in one arrhythmia, such as ventricular tachycardia (VT) growing from low risk to high risk).

SUMMARY OF THE DISCLOSURE

The present disclosure provides a more objective and reliable approach and application for medical electrophysiological signal analysis with better signal noise ratio (SNR) and accuracy. The disclosed system and method may solve the aforementioned shortcoming and therefore improve the performance and clinical application of the current cardiac arrhythmia analysis and detection.

A method for predicting cardiac arrhythmia, comprising monitoring patient data elements, the data elements comprising a data stream; performing symbolization of the data stream; performing a symbolic complexity calculation on the symbolized data; comparing information obtained from the symbolic complexity calculation to a predetermined threshold; and providing information to a user if the information obtained from the symbolic complexity calculation exceeds the predetermined threshold.

A system for predicting cardiac arrhythmia, comprising: means for monitoring patient data elements, the data elements comprising a data stream; means for performing symbolization of the data stream; means for performing a symbolic complexity calculation on the symbolized data; means for comparing information obtained from the symbolic complexity calculation to a predetermined threshold; and means for providing information to a user if the information obtained from the symbolic complexity calculation exceeds the predetermined threshold.

A machine readable storage device tangibly embodying a series of instructions executable by the machine to perform a series of steps, the steps comprising: monitoring patient data elements, the data elements comprising a data stream; performing symbolization of the data stream; performing a symbolic complexity calculation on the symbolized data; comparing information obtained from the symbolic complexity calculation to a predetermined threshold; and providing information to a user if the information obtained from the symbolic complexity calculation exceeds the predetermined threshold.

BRIEF DESCRIPTION OF THE DRAWINGS

The accompanying drawings illustrate preferred embodiments of the disclosure so far devised for the practical application of the principles thereof, and in which.

DETAILED DESCRIPTION

Complexity Characterization and Arrhythmia Differentiation

Figure 1:
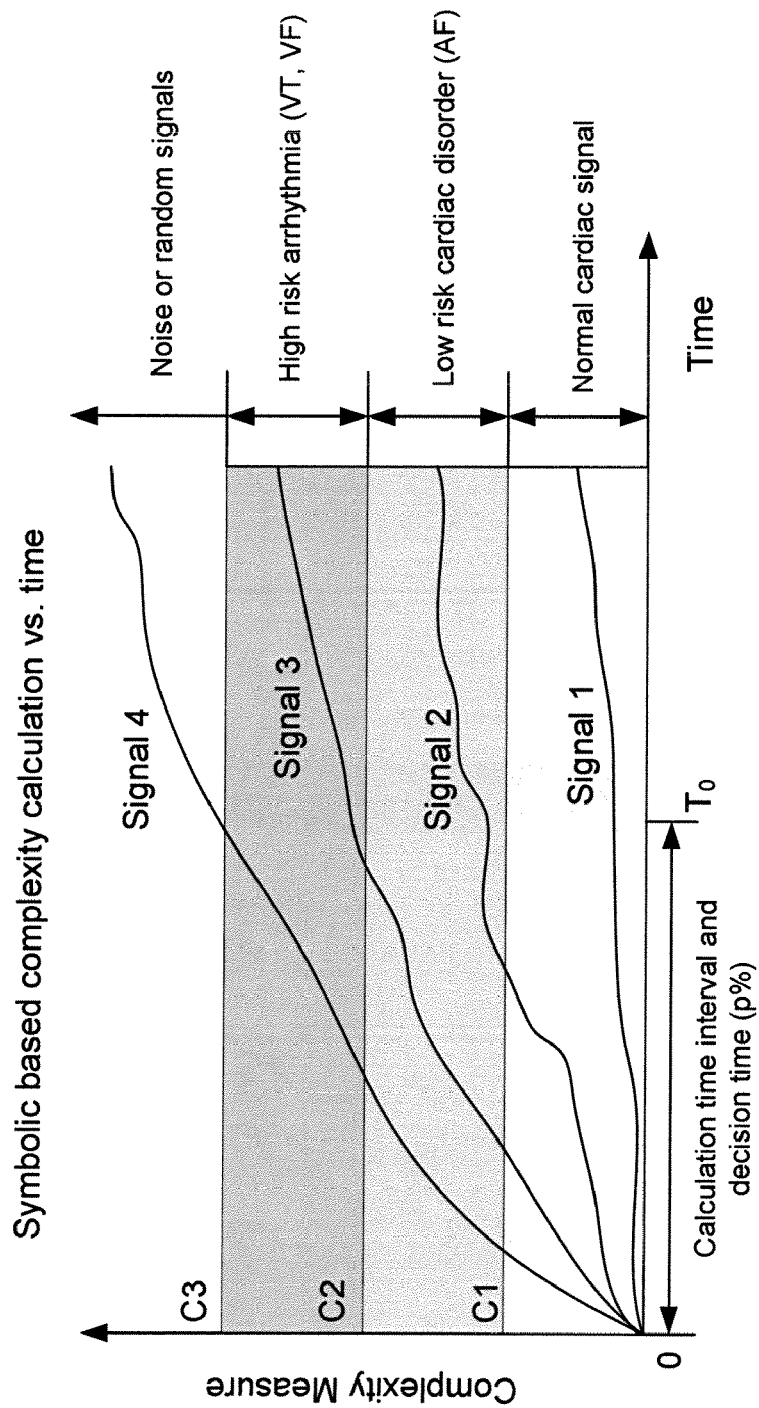
FIG. 1 illustrates the symbolic dynamics based complexity calculation and characterization of cardiac arrhythmia signals.

Cardiac electrophysiological signals analyses, especially surface ECG and intra-cardiac electrograms, are essential to qualitatively and quantitatively test and evaluate heart activity and abnormality. FIG. 1 shows a symbolic dynamics-based complexity calculation and characterization of different cardiac pathologies. For example, the complexity index value of normal cardiac signals is from 0 to C1. Low risk order from C1 to C2, high risk arrhythmia are from C2 to C3, and an index above C3 indicates noise and random signals. To indicates the time length of complexity calculation and decision for cardiac signal characterization with a statistical confidence of p %. For example, the complexity measure C(n) of the signal 1 at time $T_0$ is 0<complexity (signal 1)<C1, which indicates signal 1 belongs to normal cardiac heart signals. The complexity measurement of the cardiac signals is able to identify and categorize all kind of cardiac arrhythmias. Furthermore, the complexity calculation and monitoring can characterize and differentiate the cardiac pathologies, even differentiating the severity of two cardiac signals of the same rhythm. Although FIG. 1 shows there are four categories for cardiac rhythms, the cardiac signals can be categorized into even more types based on the specific usage and clinical application, especially for monitoring patient quality of life and safety, for patients in the operating room and in the critical care unit (CCU)/intensive care unit (ICU).

In one embodiment of the disclosure, two kinds of complexity index calculation algorithms may be used: (1) repetitive complexity, and (2) non-repetitive complexity. The repetitive complexity calculation always counts the whole string as a new mode for the complexity index. Therefore, for the same length signal, the repetitive complexity equals the non-repetitive value plus one. The non-repetitive complexity calculation may saturate if the signal is periodic, whereas the repetitive complexity measure may be linearly growing with the length of the signal. The user may select the algorithm for the signal calculation based on the application. For example, during limited length data analysis, the non-repetitive complexity calculation may be more suitable. However, if the data or signal is long and there is no saturation of the complexity calculation, it may be more appropriate to use the repetitive complexity calculation. In some embodiments of the disclosure, several complexity measurement indices can be utilized for cardiac signal characterization and differentiation as well as complexity measure C(n), such as complexity rate, complexity dispersity, complexity saturation, etc. Related algorithms and theoretical descriptions and applications are described in Lempel, A. & Ziv, J. "On the complexity of finite sequences," IEEE trans on IT.22, pages 75-81, 1976, the entirety of which is incorporated by reference herein.

Figure 2:
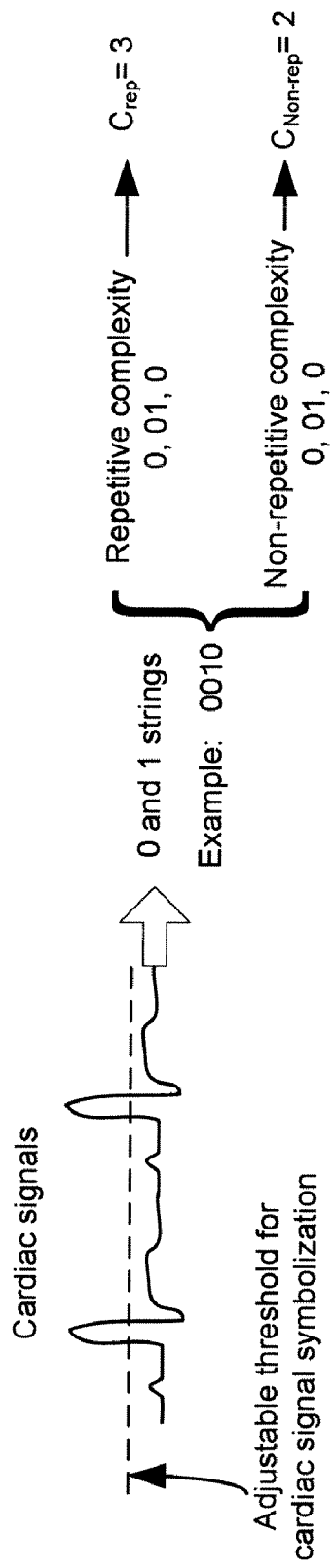
FIG. 2 illustrates and compares the two complexity calculation algorithms: repetitive complexity and non-repetitive complexity.
Figure 3:
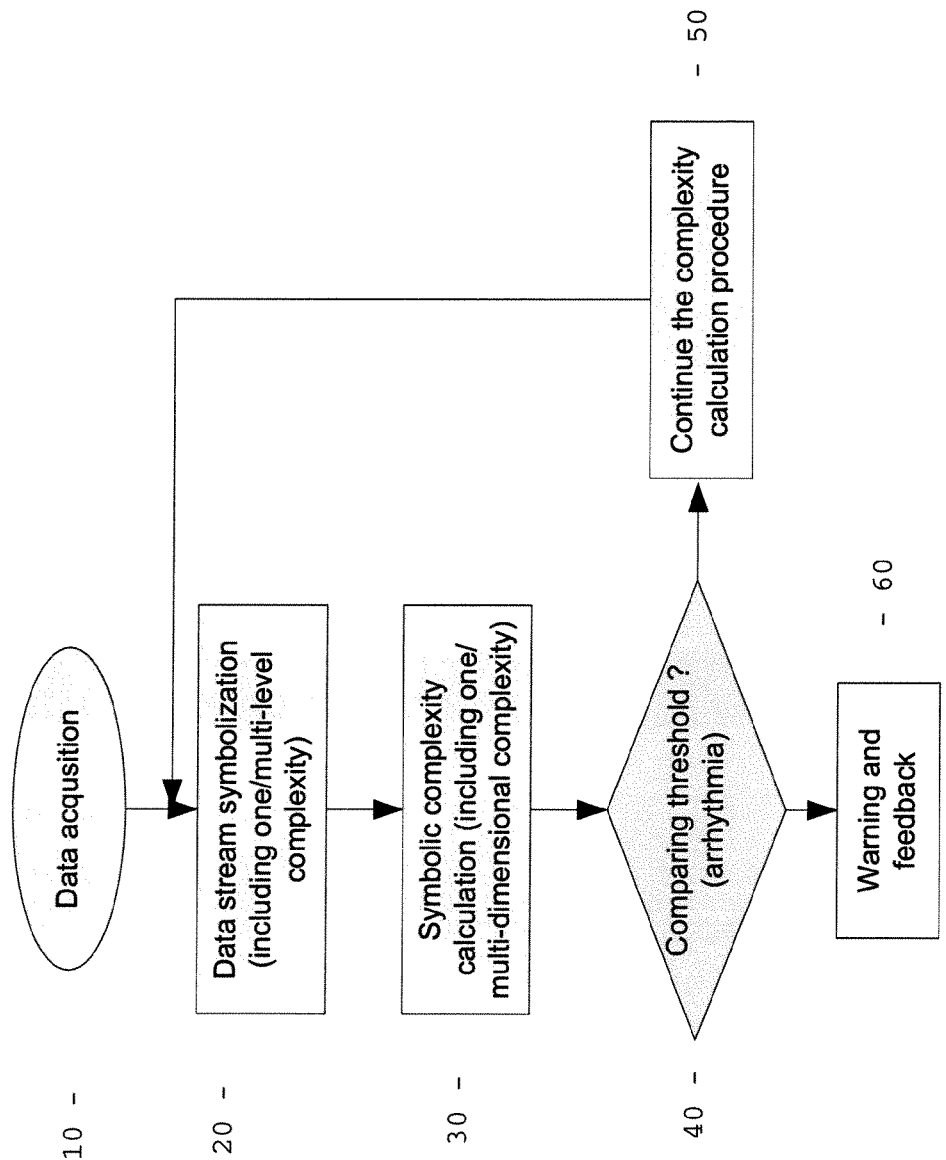
FIG. 3 is a flowchart showing the steps for calculating a complexity index.

FIG. 2 illustrates and compares the two complexity calculation algorithms: repetitive complexity and non-repetitive complexity. Repetitive complexity can be utilized to calculate the complexity rate, while non-repetitive complexity can be used to identify the saturation phenomenon. Referring to FIG. 3, steps for complexity index calculation in one embodiment of the disclosure include:

At step 10, acquire cardiac signal and perform symbolization (from signals waveform to digitized 0-1 strings);

At step 20, divide the digitized 0-1 strings into derived string $S_i$ with equal length (e.g. T0);

At step 30, perform symbolic complexity calculation of the derived string $S_i$;

At step 40, compare the output value with a threshold value signifying arrhythmia;

If the output value does not exceed the arrhythmia threshold, then at step 50 continue the complexity calculation procedure by returning to step 20 and monitoring the complexity index with time; or At step 60, provide warning and feedback if the output value exceeds the arrhythmia threshold.

If the monitoring procedure involves real-time patient monitoring, this calculation may stop under two conditions; (1) where the clinical monitoring and analysis procedure is manually terminated by a user, or (2) where the complexity calculation proceeds until no more data is provided. In this second instance, the calculation may also stop if it reaches a significant or critical value that would warrant warning the user. However, once the user confirms, the calculation may continue until no more data is provided.

It will be appreciated that FIG. 3 illustrates a generic complexity calculation analysis, and does not specify which complexity index calculation (repetitive or non-repetitive) is used.

Multi-Level Symbolic Complexity and Adaptive Ability for Index Calculation

Threshold in the cardiac signal symbolization is important as it may affect the complexity measurement resolution. Simple cardiac threshold (e.g., one fixed signal amplitude threshold for symbolization) cannot provide sufficient calculation resolution and cardiac signal detail information for arrhythmia analysis and characterization (e.g., coarse grain effects in signal symbolization, which means signal resolution is not high enough.). The disclosure presents a multi-level symbolic complexity for cardiac signals which may extract more detailed information and can help to track minute changes caused by the cardiac arrhythmia.

Figure 4:
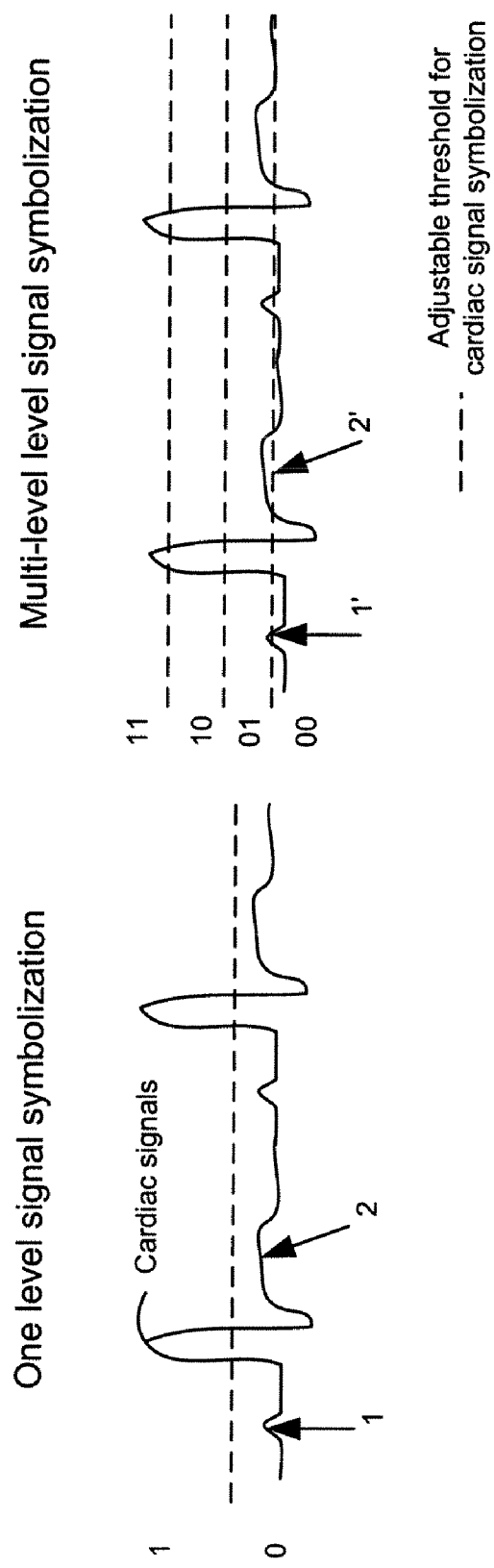
FIG. 4. illustrates the symbolization and comparison with one level threshold and multi-level threshold.

FIG. 4 shows the symbolization and comparison of multi-level and one level symbolic complexity. In the multi-level example, the cardiac signal is symbolized by 4 kinds of strings; 00, 01, 10, and 11. By contrast, with the one level signal symbolization example, the signal is converted to 0 and 1 strings which may not provide the same level of detail as those in the multi-level (two-level) signal symbolization example (e.g., 1 (1') the P wave and 2 (2') ST segment information). Thus, it will be appreciated that multi-level symbolization is a more detailed complexity analysis, which is capable of characterizing the signal into more information. For example, as can be seen, wave 1 and 2 cannot be differentiated by a one-level complexity calculation, which means that more details of the waveform are needed to calculate the difference. That is why, in FIG. 4, multi-level complexity is employed to find the ST segment changes, which could not be identified by one-level complexity calculation. As will be appreciated, the multi-level threshold strategy can be extended from one level to three levels, or to N levels for more signal information capture.

Both one level and multi-level signal symbolization strategies may employ different signal thresholds and time lengths for data to string conversion, such as 10 heart cycle length or 10 seconds. For example, if symbolization and calculation time step is 0.1 millisecond, a moving (shift) averaging window can be established to achieve an adaptive calculation mechanism that can control the averaging window size (time) and threshold for symbolization automatically or with a closed-loop feedback control. Often, for conditions without excessive noise or electrical artifacts, the preferred embodiments utilize a half range for threshold determination, (e.g. 0.5*(Max−Min) of signal amplitude in one level symbolization, (0.25, 0.5, 0.75)*(Max−Min) in two-level symbolization, and so on.)

In a noisy environment, an adaptive symbolization can be used. This adaptive symbolization mechanism can greatly increase the signal-to-noise ratio (SNR) of the symbolization stability and signal processing accuracy. For example, in a noisy environment, thresholds in two-level symbolization can be adjusted to (0.25+Δ, 0.5+Δ, 0.75+Δ)*(Max−Min) of the signal amplitude (where Δ is the maximum noise amplitude).

Multi-Dimensional Complexity and Cardiac Arrhythmia Transition/Prediction

Time domain amplitude can be utilized to achieve symbolization for signal complexity calculation and arrhythmia analysis. The signal symbolization concept can be extended to different domains, e.g. the frequency domain. The frequency spectrum and power spectrum of the signal can also be utilized for symbolization and then calculation of the cardiac signal complexity and irregularity. The signal symbolization and complexity estimation can be used in time domain as well as frequency domain. Furthermore, a multi-dimensional complexity analysis can be constructed for arrhythmia identification, rhythm transition tracking and risky pathology prediction.

Figures 5A, 5B, 5C:
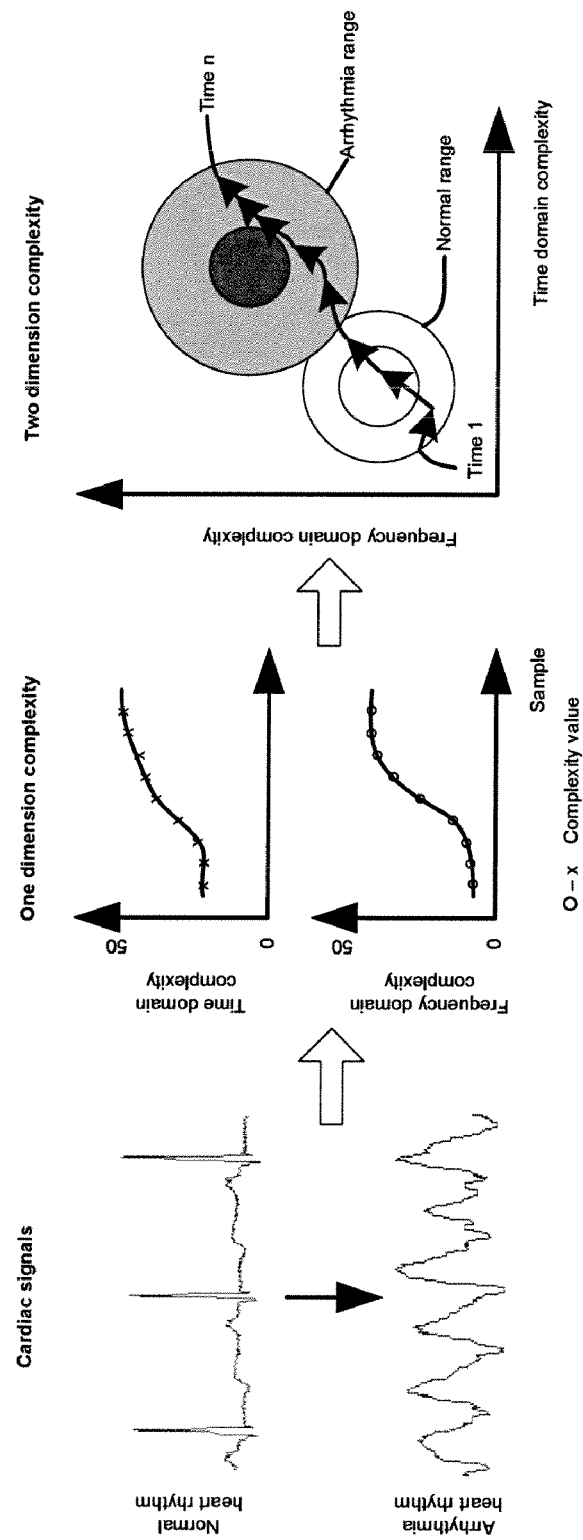
FIGS. 5A-5C illustrate an example for multi-dimensional complexity calculation of cardiac electrophysiology activity from a normal rhythm to arrhythmia.

Practically, there are a variety of ways to accomplish warning and feedback to the user and patient. For example, the complexity calculation may be presented in the control room monitoring screen and the nurse may be made aware of what is occurring for each monitored patient. This information may go directly to a data recording device, information server system and/or a logging system. At the same time, this information may be displayed in the operating room screen for a doctor to use. Different colors can be used for the displayed information to signify varying severity or criticality of patient condition. Also, audible warnings may be implemented to warn technicians, nurses and/or doctors of particularly important conditions and events, For example, FIGS. 5A-C demonstrate an example of cardiac rhythm transition, from normal heart beat to arrhythmia (FIG. 5A). One dimension and two dimension complexity calculations (time domain/frequency domain) show the cardiac rhythm transition from the normal to arrhythmia. Compared with one dimensional complexity analysis (FIG. 5B), two dimensional complexity mapping (FIG. 5C) provides better visualization for changes and transition procedure of the cardiac rhythm as well as prediction of the risks.

In FIGS. 5A-C, there are two separate regions which stand for different cardiac rhythms, one for normal and one for severe cardiac arrhythmias. During monitoring, if the complexity calculation of the recording data and signal is showing a trend from normal to severe region, this indicates there is some possibility that cardiac arrhythmia is going to occur. If the complexity calculation keeps changing and a mapping edge threshold (e.g., edge of the circle) is passed, then it is predicted that the cardiac pathology is imminent even though it has not yet happened. This is termed "prediction value," and based on the region switching analysis and qualification, early diagnosis and clinical decision making can be achieved.

It will be appreciated that in FIG. 5B, "sample" stands for the complexity calculation point of shift averaging window for the cardiac signals.

In the example, two dimensional symbolic complexity calculation and mapping are used to identify the two rhythms and the gradual arrhythmia transition. In two dimensional arrhythmia mapping (FIG. 5C), each mapping point stands for the combination of the time domain complexity and frequency domain complexity for the same averaging windowed signal. By using the two dimensional mapping, cardiac rhythm transition and trend can be identified and predicted. The two dimension complexity mapping in FIG. 5C also shows the two cone areas for different rhythms, which indicate the criteria for the cardiac rhythm identification, differentiation and transition. Hence, a risk threshold and warning strategy can be set up for a clinician and even automatic treatment, especially in the CCU and ICU. As previously noted, warning and arrhythmia feedback can be provided in a variety of visual and audible forms. Additionally, a map-based warning may be provided in the configuration of FIG. 5C. A map such as that of FIG. 5C may be used as a two-dimensional feedback and graphic-based warning for a user, such as a nurse or doctor.

The signal symbolization and complexity calculation based arrhythmia identification and detection is a new mapping method for transferring the cardiac signals into a different kind of domain, through which the arrhythmia and minute cardiac pathology can be earlier, more accurately, and more reliably captured and detected. In one embodiment of the present disclosure, a multi-level symbolization based multi-dimension complexity analysis is used for electrophysiological signal monitoring and analysis. It will be appreciated, however, that the application of the disclosed technique is not limited to symbolic complexity, and thus other analysis strategies can also be utilized for the comprehensive calculation purpose, such as time/frequency entropy, fraction dimension, and other linear and nonlinear calculation indices for arrhythmia analysis and characterization. At the same time, the disclosed symbolization strategies and complexity calculations can be utilized in other application, such as hemo and vital sign signal analysis and warning.

Exemplary Symbolic Complexity Definition

The complexity calculation procedure begins when monitoring begins. Windowed data is derived and a string achieved. The complexity calculation thus begins. A moving window for calculation is employed as described in FIG. 6. For simplicity, the disclosure has only considered 0-1 strings $s_1 s_2 \ldots s_n$ ($s_i$ is character 0 or 1, i=1, 2 . . . , n). Let S, Q denote, respectively, two strings, and SQ be the concatenation of S and Q, while string SQπ is derived from SQ after its last character is deleted (π means the operation to delete the last character). Let v(SQπ) denote the vocabulary of all different substrings of SQπ. At the beginning, c(n)=1, S=$s_1$, Q=$s_2$, therefore, SQπ=$S_1$. For generalization, now suppose S=$s_1 s_2 \ldots s_r$, Q=$s_{r+1}$; if Q∈v(SQπ), then $s_{r+1}$ is a substring of $s_1 s_2 \ldots s_r$, therefore S doesn't change, and renew Q to be $s_{r+1} s_{r+2}$, then judge if Q belongs to v(SQπ) or not; and doing so in this way until Q∉v(SQπ), now suppose Q=$s_{r+1} s_{r+2} \ldots s_{r+i}$, which is not a substring of $s_{1s2} \ldots s_{rsr+1} \ldots s_{r+i+1}$, thus increase c(n) by one. Thereafter combine S with Q and S is renewed to be S=$s_1 s_2 \ldots s_r s_{r+1} \ldots s_{r+i}$, while take Q as Q=$s_{r+i+1}$. Repeat above procedures until Q is the last character, at this time the number of different substrings of $s_1 s_2 \ldots s_n$ is c(n), i.e, the measure of complexity. Obviously, only by two simple operations of comparison and accumulation, the computation of c(n) is very easy to implement.

Complexity Information Theory

The information extracted from the coarse-grain symbol dynamic sequences was limited, and speed information could not be obtained by just complexity measurements. In abnormal cardiac signal analysis, the clinician hope to get accurate pathological information, such as body fluid and nerve control interdiction, as well as the abnormal cardiac signal extraction. The extracted complexity rate information can construct a correct and reasonable relationship between pathology and diagnosis parameters. On the basis of established complexity measures and the complexity method of extracted system features, the preferred embodiments present a method for complexity study: the symbolic dynamic system complexity rate information. The underlying cause of non-stationary dynamic change can be uncovered with the help of this method.

Given a dynamic system time sequence $X=\{x_1, x_2, \ldots x_i, \ldots\}$, there exists subsequence $L_i$, $L_i=\{x_1, x_2, \ldots, x_i\}$, in which $i=1, 2, \ldots, n$;

Utilizing the Lempel-Ziv (L-Z) complexity, corresponding complexity can be computed for each subsequence $L_i$; $L_i$ is corresponding to complexity $c_i$.

Figure 6:
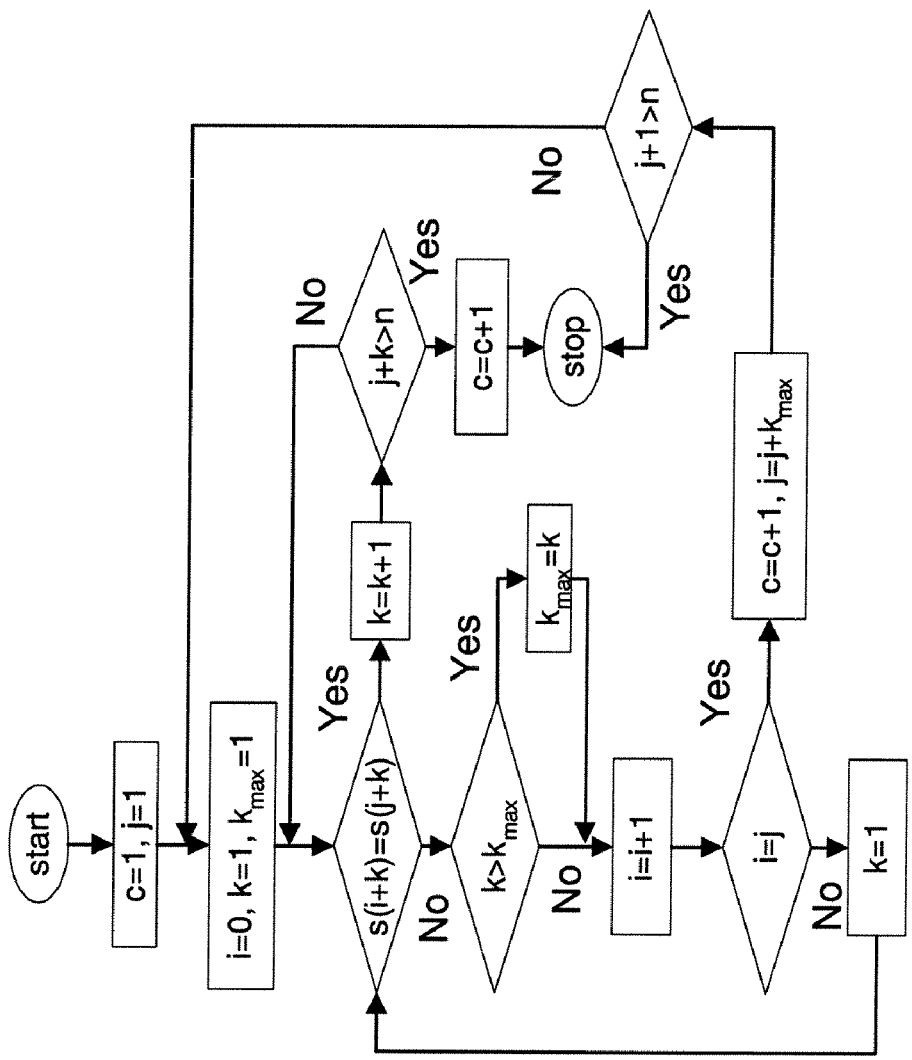
FIG. 6 illustrates an exemplary algorithm structure schematic of the complexity calculation of symbolic strings.

We now refer to FIG. 6.

C.1. Definition (Finite Sequence Complexity)

Support sequence $X=\{x_1, x_2, \ldots x_i, \ldots\}$, there exists subsequence $L_i$, $L_i=\{x_1, x_2, \ldots, x_i\}$, in which $i=1, 2, \ldots n$; we define $c_n=\{c_1, c_2, \ldots, c_n\}$ as the corresponding complexity measure sequence of the sequence $X_n$, in which $c_i$ is the sequence complexity of the $L_i$, $X_n$ is the finite time sequence of X.

C.2. Definition (Time Sequence Complexity Rate)

Given a finite time sequence $X=\{x_1, x_2, \ldots, x_i, \ldots\}$, the corresponding finite complexity sequence is $c=\{c_1, c_2, \ldots, c_n\}$, we define complexity as follows:

$$cc(n) = \frac{c_{n_1} - c_{n_j}}{n_i - n_j}$$

in which $n_i, n_j$ must be at least larger than Takens' embedding dimension in order to avoid spurious computation. $cc(n)$ reflects the speed of the complexity change of the finite time sequence.

According to this definition, the complexity rate of the whole time sequence $X(n)$ can be calculated from slope rate of the sequence fitting polynomial:

$$cc[x(n)] = \mathrm{DIFF}[x(n)]$$

Based on the definition above, it is deduced:

C.2.1 when the time sequence is an infinite subsequence of a stochastic procedure, the corresponding maximum complexity is infinite and the complexity rate is 1.

C.2.2 when the time sequence is a finite subsequence of a stochastic procedure, the corresponding maximum complexity is a finite value and the complexity rate is 1.

C.2.3 when the time sequence is a subsequence of a periodic procedure, the corresponding complexity of the infinite subsequence is equal to that of finite effective sequence and is a finite value. (Here the finite effective subsequence means that the length of the time sequence is enough for the effective complexity computation). That is, given a periodic time sequence $X=\{x_1, x_2, \ldots, x_i, \ldots\}$, there exists a constant N, when $i>N$, such that:

$cc(i)=c$, in which the constant $c$ is a finite value.

(Note that: to achieve algorithm standard and ease of comparison, the computing complexity of the time sequence has been standardized.)

C.2.4 when the time sequence is the output of a deterministic chaotic system, the corresponding complexity of its subsequence increases with the time series length. And if the corresponding complexity rate is $cc(n)_{chaos}$, then the $cc(n)_{chaos}$ is less than 1. And $cc(n)_{chaos}$ increases with the number of chaotic system dimension.

C.2.5 given a discrete time series of an arbitrary continuous deterministic chaotic system or a random system and the corresponding symbolic series complexity rate is $cc_m$, the maximum complexity can be approximately computed as follows:

$c_x = cc_m \cdot l(x)$ in which the $c_x$ is the time sequence complexity and the $l(x)$ is the length of the symbol series. (here we utilize the linear fitting)

C.3. Average Complexity

Given a limited dynamic time sequence $X=\{x_1, x_2, \ldots, x_n\}$, in which $n<\infty$; the corresponding complexity sequence is $c_x=\{c_1, c_2, \ldots, c_n\}$, Then:

$$\overline{c_x} = \lim_{n \to \infty} \frac{1}{N} \sum_{i=1}^{n} c_i$$

Suppose the original procedure is continuous, the corresponding average complexity:

$$\overline{c_x} = \frac{1}{T} \int_0^T cc_1 dx$$

Advantages of the Disclosure

In summary, the disclosure may provide following advantages over the current clinical approaches and research methods:

More objective analysis and detection of the cardiac arrhythmia with numerical calculation index and characterization of the pathologies.

Multi-level symbolization and calculation of the electro-physiological signal can provide better reliability and analysis resolution for identifying the cardiac disorders, differentiating cardiac arrhythmias, characterizing the pathological severities, with higher sensitivity.

Adaptive analysis of the cardiac signal complexity enables calculation efficiency and reliability with high SNR, and with low calculation volume and power consumption.

One dimension (time domain complexity or frequency domain complexity) and multi-dimension (such as two dimensional time-frequency complexity mapping) symbolic analysis may provide more information of cardiac pathology and high risk rhythm transition to doctors.

Symbolic complexity analysis and algorithm are capable of predicting the growing trend of the cardiac arrhythmia, pathological severity indication, and warning.

Theoretically, the disclosed system and method are not limited to any particular hardware, and can be integrated into any of a variety of patient monitoring systems. For example, a device and system for accomplishing the disclosed complexity analysis and calculation method may include sensors for patient signal acquisition (e.g., leads for surface ECG and catheter for intra-cardiac electrograms), data conditioning and digitization elements, a data analysis module, and an information processing and warning module. The front-end electronics for data signal acquisition including data symbolization, complexity calculations, and severity analysis can be implemented in software, or in hardware (such as digital signal processors (DSP) or field programmable gate array (FPGA) algorithm and processing).

The system and technique described herein may be automated by, for example, tangibly embodying a program of instructions upon a computer readable storage media, capable of being read by machine capable of executing the instructions. A general purpose computer is one example of such a machine. Examples of appropriate storage media are well known in the art and would include such devices as a readable or writeable CD, flash memory chips (e.g., thumb drive), various magnetic storage media, and the like.

The exemplary features of the system and technique have been disclosed, and further variations will be apparent to persons skilled in the art. All such variations are considered to be within the scope of the appended claims. Reference should be made to the appended claims, rather than the foregoing specification, as indicating the true scope of the subject system and technique.

What is claimed is:

1. A method for predicting cardiac arrhythmia, comprising acquiring patient data elements comprising a patient cardiac signal, the data elements comprising a data stream; establishing a window within the data stream; performing symbolization of data in the data stream window into multi-level symbols individually represented by a plurality of bits; performing a symbolic complexity calculation on the symbolized data; comparing information obtained from the symbolic complexity calculation to a plurality of predetermined thresholds associated with different levels of complexity and corresponding different levels of risk or severity of a medical condition; and providing information to a user if the information obtained from the symbolic complexity calculation exceeds the predetermined thresholds.

2. The method of claim 1, including adaptively dynamically varying said thresholds in response to signal noise.

3. The method of claim 2, wherein the step of performing symbolic complexity calculation on the symbolized data comprises a multi-level complexity calculation.

4. The method of claim 1, including adaptively dynamically varying said window in response to signal noise.

5. The method of claim 4, wherein the step of providing information to a user comprises providing an audible or visual alarm to the user if the information obtained from the symbolic complexity calculation exceeds a predetermined threshold.

6. The method for predicting cardiac arrhythmia, comprising
monitoring patient data elements comprising patient cardiac signals, the data elements comprising a data stream;
performing symbolization of the data stream comprising a multi-level symbolization;
performing a symbolic complexity calculation comprising a multi-level complexity calculation on the symbolized data;
comparing information obtained from the symbolic complexity calculation to a predetermined threshold; and
providing information to a user if the information obtained from the symbolic complexity calculation exceeds the predetermined threshold wherein the step of providing information to a user further comprises:
providing a graphical display of frequency domain complexity vs. time domain complexity, the graphical display comprising a predetermined visible normal region associated with normal cardiac signals and a predetermined visible severe region associated with cardiac signals indicative of arrhythmia; and
mapping the complexity calculation on the graphical display to provide a visual indication to a user that the cardiac signals are: (a) within the normal region, (b) are approaching the severe region, or (c) are within the severe region.

7. The method of claim 6, wherein the complexity calculation is mapped on the graphical display over time to provide a visible trending of the cardiac signals, the method further comprising providing a risk threshold that identifies to a user when the cardiac signals are trending to the severe region.

8. A machine readable storage device tangibly embodying a series of instructions executable by a machine comprising at least one computer to perform a series of steps for predicting cardiac arrhythmia, the steps comprising:
acquiring patient data elements comprising a patient cardiac signal, the data elements comprising a data stream;
establishing a window within the data stream;
performing symbolization of data in the data stream window into multi-level symbols individually represented by a plurality of bits;
performing a symbolic complexity calculation on the symbolized data;
comparing information obtained from the symbolic complexity calculation to a plurality of predetermined thresholds associated with different levels of complexity and corresponding different levels of risk or severity of a medical condition; and
providing information to a user if the information obtained from the symbolic complexity calculation exceeds the predetermined thresholds.

9. The machine readable storage device of claim 8, including adaptively dynamically varying said thresholds in response to signal noise.

10. The machine readable storage device of claim 9, wherein the step of performing symbolic complexity calculation on the symbolized data comprises a multi-level complexity calculation.

11. The machine readable storage device of claim 10, including adaptively dynamically varying said window in response to signal noise.

12. A machine readable storage device tangibly embodying a series of instructions executable by a machine to perform a series of steps, the steps comprising:
employing at least one computer for,
monitoring patient data elements comprising patient cardiac signals, the data elements comprising a data stream;
performing symbolization of the data stream comprising a multi-level complexity calculation;
performing a symbolic complexity calculation on the symbolized data comprising a multi-level complexity calculation;
comparing information obtained from the symbolic complexity calculation to a predetermined threshold; and
providing information to a user if the information obtained from the symbolic complexity calculation exceeds the predetermined threshold wherein the step of providing information to a user further comprises:
providing a graphical display of frequency domain complexity vs. time domain complexity, the graphical display comprising a predetermined visible normal region associated with normal cardiac signals and a predetermined visible severe region associated with cardiac signals indicative of arrhythmia; and
mapping the complexity calculation on the graphical display to provide a visual indication to a user that the cardiac signals are: (a) within the normal region, (b) are approaching the severe region, or (c) are within the severe region.

13. The machine readable storage device of claim 12, wherein the complexity calculation is mapped on the graphical display over time to provide a visible trending of the cardiac signals, the method further comprising providing a risk threshold that identifies to a user when the cardiac signals are trending to the severe region.

* * * * *